United States Patent
Müller

[11] Patent Number: 5,886,176
[45] Date of Patent: Mar. 23, 1999

[54] PROCESS FOR PREPARING SULPHONYLUREA SALTS

[75] Inventor: Klaus-Helmut Müller, Düsseldorff, Germany

[73] Assignee: Bayer Aktiengesellschaft, Leverkusen, Germany

[21] Appl. No.: 24,571

[22] Filed: Mar. 1, 1993

[30] Foreign Application Priority Data

Mar. 5, 1992 [DE] Germany ............... 42 06 918.1
Nov. 19, 1992 [DE] Germany ............... 42 39 002.8

[51] Int. Cl.⁶ .................. C07D 251/02; C07D 251/26
[52] U.S. Cl. .................. 544/219; 544/215; 544/216; 544/206; 544/207; 544/208; 544/209; 544/211; 544/212; 544/320; 544/321; 544/323; 544/324; 544/331; 544/332
[58] Field of Search .................. 544/211, 212, 544/206, 207, 208, 209, 320, 321, 323, 324, 331, 332, 219

[56] References Cited

U.S. PATENT DOCUMENTS 4,690,707  9/1987  Föry et al. ................. 544/209
4,849,010  7/1989  Hillemann ................. 544/321

FOREIGN PATENT DOCUMENTS 2032398  6/1991  Canada .
0101670  8/1983  Germany .
3609700  11/1987  Germany .
0304282  8/1988  Germany .
0433779  12/1990  Germany .

OTHER PUBLICATIONS

Chemical Abstract, vol. 108:70631d, 1988.
Chemical Abstract, vol. 101:38480y, 1984.

*Primary Examiner*—John M. Ford
*Assistant Examiner*—Pavanaram K. Sripam
*Attorney, Agent, or Firm*—Sprung Kramer Schaefer & Briscoe

[57] ABSTRACT

The invention relates to a novel process for preparing herbicidal sulphonylurea salts of the formula (I)

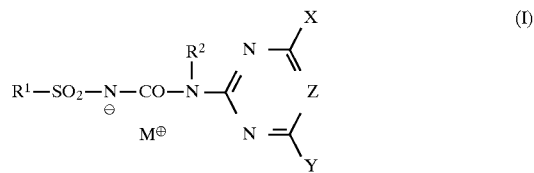

in which $M^+$ represents an alkali metal ion or an alkaline earth metal ion equivalent, Z represents N, CH or C-halogen, $R^1$ represents in each case optionally substituted aryl, aralkyl or heteroaryl, (where $R^2$, X and Y have the meanings given in the description).

11 Claims, No Drawings

PROCESS FOR PREPARING SULPHONYLUREA SALTS

The invention relates to a novel process for preparing sulphonylurea salts which can be used as herbicides.

It is known that sulphonylurea salts are obtained if solutions of sulphonylureas in halogenated hydrocarbon solvents are reacted with alkali metal hydroxides or alkaline earth metal hydroxides and, optionally after filtration, the solvent is distilled off (cf. EP-A 304 282).

Since crystallisation of a product from the solution does not generally take place in this procedure, an energy-intensive distillation of the solvent is necessary and there is scarcely any chance of achieving a purification effect.

It is known, additionally, that sulphonylurea salts can be obtained in good yields and in high purity by reacting sulphonylureas with alkali metal hydroxides or with basic organic nitrogen compounds in the presence of hydrocarbons as diluents (cf. EP-A 433779).

It has now been found that sulphonylurea salts of the general formula (I)

$$R^1-SO_2-\underset{\ominus}{N}-CO-\underset{M^\oplus}{\overset{R^2}{N}}-\underset{N}{\overset{N}{\diagdown}}\overset{X}{\underset{Y}{\diagup}}Z \quad (I)$$

in which

M$^+$ represents an alkali metal ion or an alkaline earth metal ion equivalent,

R$^1$ represents in each case optionally substituted aryl, aralkyl or heteroaryl, R$^2$ represents hydrogen or in each case optionally substituted alkyl, alkenyl, alkinyl or aralkyl, X represents hydrogen, halogen or alkyl, alkoxy, alkylthio or alkylamino, in each case optionally substituted by halogen or alkoxy, Y represents hydrogen, halogen or alkyl or alkoxy, in each case optionally substituted by halogen, and Z represents nitrogen, a CH grouping or a C-halogen grouping, are obtained in very good yields and in high purity, if sulphonamides of the general formula (II)

$$R^1-SO_2-NH_2 \quad (II)$$

in which

R$^1$ has the abovementioned meaning, are first reacted with alkali metal hydroxides or alcoholates or with alkaline earth metal hydroxides or alcoholates optionally in the presence of a diluent at temperatures between -20° C. and +150° C. (step 1) and the sulphonamide salts thus formed, of the general formula (IIa)

$$R^1-SO_2-NH-M^+ \quad (IIa)$$

in which

M and R$^1$ have the abovementioned meaning, are then reacted with urethanes (carbamates) of the general formula (III)

$$R^3-O-CO-\underset{}{\overset{R^2}{N}}-\underset{N}{\overset{N}{\diagdown}}\overset{X}{\underset{Y}{\diagup}}Z \quad (III)$$

in which

R$^2$, X, Y and Z have the abovementioned meaning and

R$^3$ represents alkyl, aralkyl or aryl, optionally in the presence of a diluent at temperatures between -20° C. and +150° C. (step 2) and the products of the formula (I) are isolated by conventional methods.

It is to be regarded as surprising that the preparation of sulphonylurea salts succeeds in very good yields and in high purity, starting from the sulphonamides of the formula (II) and the urethanes of the formula (III), without intermediate isolation of the corresponding free sulphonylureas, and where the reservations regarding the diluents which can be used are overcome (cf. EP-A 433779).

The process according to the invention relates preferably to the preparation of sulphonylurea salts of the formula (I), in which M$^+$ represents a lithium, sodium or potassium ion, or a magnesium or calcium ion equivalent, R$^1$ represents in each case optionally substituted phenyl, naphthyl, benzyl, pyridyl, thienyl or pyrazolyl, where the possible substituents are preferably selected from the series halogen, carboxyl, cyano, carbamoyl, nitro, amino, $C_1$–$C_4$-alkyl, $C_1$–$C_4$-halogenoalkyl, $C_1$–$C_4$-alkoxy-$C_1$–$C_4$-alkyl, $C_1$–$C_4$-alkoxy, $C_1$–$C_4$-halogenoalkoxy, $C_1$–$C_4$-alkoxy-$C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)-amino-sulphonyl, N-$C_1$–$C_4$-alkoxy-N-$C_1$–$C_4$-alkyl-amino-sulphonyl, phenyl, phenoxy, $C_1$–$C_4$-alkoxy-carbonyl, $C_1$–$C_4$-halogenoalkoxycarbonyl, $C_1$–$C_2$-alkoxy-$C_1$–$C_2$-alkoxy-carbonyl, di-($C_1$–$C_4$-alkyl)-amino-carbonyl, R$^2$ represents hydrogen, $C_1$–$C_6$-alkyl (which is optionally substituted by fluorine, cyano, $C_1$–$C_4$-alkoxy or $C_1$–$C_4$-alkylthio), $C_3$–$C_6$-alkenyl and $C_3$–$C_6$-alkinyl (which are optionally substituted by fluorine or chlorine) or phenyl-$C_1$–$C_2$-alkyl (which is optionally substituted in the phenyl moiety by fluorine, chlorine, nitro, cyano, methyl, methoxy or $C_1$–$C_2$-alkoxycarbonyl), X represents hydrogen, halogen or $C_1$–$C_4$-alkyl, $C_1$–$C_4$-alkoxy, $C_1$–$C_4$-alkylthio or $C_1$–$C_4$-alkylamino, in each case optionally substituted by halogen or $C_1$–$C_4$-alkoxy, Y represents hydrogen, halogen or $C_1$–$C_4$-alkyl or $C_1$–$C_4$-alkoxy, in either case optionally substituted by halogen, and Z represents nitrogen or a CH grouping.

The process according to the invention relates in particular to the preparation of sulphonylurea salts of the formula (I), in which M$^+$ represents a sodium ion or a potassium ion, R$^1$ represents phenyl or benzyl, in either case substituted in the ortho position by fluorine, chlorine, bromine, methyl, ethyl, trifluoromethyl, methoxy, ethoxy, difluoromethoxy, trifluoromethoxy, chloroethoxy, methoxyethoxy, ethoxyethoxy, methylthio, ethylthio, propylthio, methylsulphinyl, ethylsulphinyl, propylsulphinyl, methylsulphonyl, ethylsulphonyl, propylsulphonyl, dimethylaminosulphonyl, diethylaminosulphonyl, N-methoxy-N-methyl-aminosulphonyl, phenyl, methoxycarbonyl, ethoxycarbonyl, propoxycarbonyl, isopropoxycarbonyl, chloroethoxycarbonyl, methoxyethoxycarbonyl, dimethylaminocarbonyl or diethylaminocarbonyl and optionally in a further position by halogen, or represents 3-dimethylaminocarbonyl-pyridin-2-yl or 3-ethylsulphonyl-pyridin-2-yl, 2-methoxycarbonyl-thiophen-3-yl or 1-methyl-4-methoxycarbonyl-pyrazol-5-yl, 1-methyl-4-ethoxycarbonyl-pyrazol-5-yl, 1-methyl-3-chloro-4-methoxycarbonyl-pyrazol-5-yl, 1-methyl-3-chloro-4-ethoxycarbonyl-pyrazol-5-yl or 1-pyridyl-4-methoxycarbonyl-pyrazol-5-yl, $R^2$ represents hydrogen or methyl, X represents hydrogen, chlorine, methyl, ethyl, trichloromethyl, trifluoromethyl, methoxymethyl, methoxy, ethoxy, difluoromethoxy, fluoroethoxy, difluoroethoxy, trifluoroethoxy, methoxyethoxy, methylthio, ethylthio, methylamino or ethylamino, Y represents hydrogen, chlorine, methyl, ethyl, trifluoromethyl, methoxy, ethoxy or difluoromethoxy, and Z represents nitrogen or a CH grouping.

If, for example, 2-difluoromethoxy-benzenesulphonamide and sodium methylate are used as starting materials, and the sodium salt thus formed is reacted with phenyl N-methyl-N-(4,6-dimethoxy-1,3,5-triazine-2-yl)-carbamate, the course of the reaction in the process according to the invention can be outlined by the following reaction scheme:

The sulphonamides to be used as starting materials in the process according to the invention are defined generally by the formula (II). In formula (II), $R^1$ has preferably or in particular that meaning which was already indicated above, in connection with the description of the compounds of the formula (I) to be prepared according to the invention, as particularly preferred for $R^1$.

Examples of the starting materials of the formula (II) which may be mentioned are:

2-fluoro-, 2-chloro-, 2-bromo-, 2,5-dichloro-, 2,6-dichloro-, 2-nitro-, 2-cyano-, 2-methyl-, 2-trifluoromethyl-, 2-methoxy-, 2-methoxy-, 2-difluoromethoxy-, 2-trifluoromethoxy-, 2-methylthio-, 2-ethylthio-, 2-(2-chloro-ethoxy)-,2-(2-methoxy-ethoxy)-, 2-dimethylaminosulphonyl-, 2-phenyl-, 2-methoxycarbonyl-, 2-ethoxycarbonyl- and 2-propoxycarbonyl-benzenesulphonamide, (2-chloro-phenyl)-, (2-difluoromethoxy-phenyl)-, (2-trifluoromethoxy-phenyl)-, (2-methoxycarbonyl-phenyl)- and (2-ethoxycarbonyl-phenyl)-methanesulphonamide, 3-dimethylaminocarbonyl-pyridine-2-sulphonamide, 3-ethylsulphonyl-pyridine-2-sulphonamide, 2-methoxycarbonyl-thiophene-3-sulphonamide, 1-methyl-4-methoxycarbonyl-, 1-methyl-4-ethoxycarbonyl-, 1-methyl-3-chloro-4-methoxycarbonyl-, 1-methyl-3-chloro-4-ethoxycarbonyl- and 1-pyridyl-4-methoxycarbonyl-pyrazole-5-sulphonamide.

The sulphonamides of the formula (II) are known and/or may be prepared by processes known per se (cf. J. Org. Chem. 25 (1960), 1824; loc. cit. 33 (1968), 2104; DE-AS (German Published Specification) 2308262; EP-A 23140;

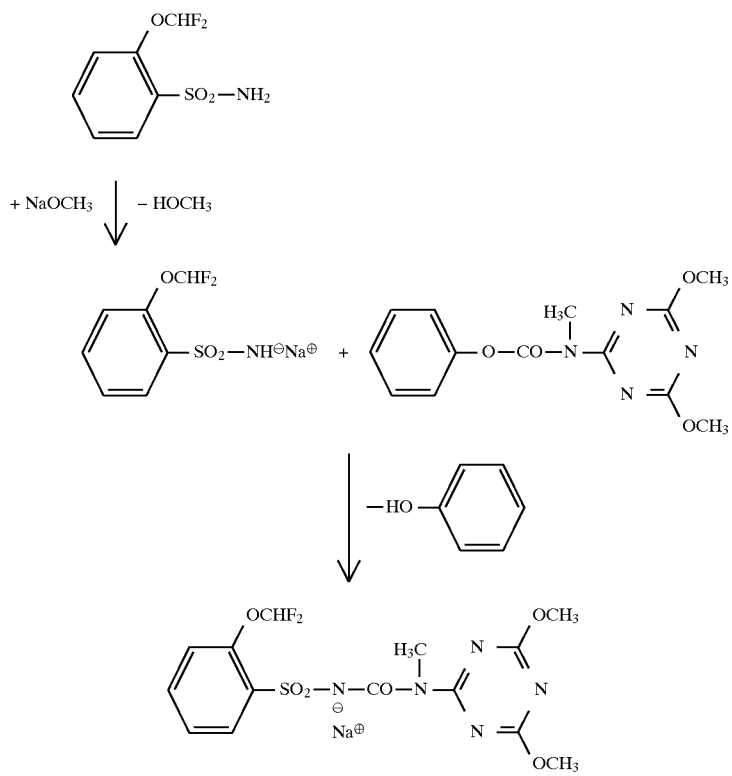

EP-A 23141; EP-A 23422; EP-A 35893; EP-A 48143; EP-A 51466; EP-A 64322; EP-A 70041; EP-A 44808; EP-A 44809; U.S. Pat. No. 2,929,820; U.S. Pat. No. 4,282,242; U.S. Pat. No. 4,348,220; U.S. Pat. No. 4,372,778; U.S. Pat. No. 4,806,147).

The urethanes to be used additionally as starting materials in the process according to the invention for preparing compounds of the formula (I) are generally defined by the formula (III).

In formula (III), $R^2$, X, Y and Z have preferably or in particular those meanings which were already indicated above, in connection with the description of the compounds of the formula (I) which can be prepared according to the invention, as preferred or particularly preferred for $R^2$, X, Y and Z;

$R^3$ preferably represents methyl, ethyl, benzyl or phenyl, in particular phenyl.

Examples of the starting materials of the formula (III) which may be mentioned are:

N-(4,6-dimethyl-pyrimidin-2-yl)-, N-(4-methoxy-6-methylpyrimidin-2-yl)-, N-(4,6-dimethoxy-pyrimidin-2-yl)-, N-(4,6-dimethyl-s-triazin-2-yl)-, N-(4-methoxy-6-methyl-s-triazin-2-yl)- and N-(4,6-dimethoxy-s-triazin-2-yl)-N-methyl-O-methyl-urethane, -N-methyl-O-ethyl-urethane, -N-methyl-O-benzyl-urethane and -N-methyl-O-phenyl-urethane.

The starting materials of the formula (III) are known and/or may be prepared by processes known per se (cf. EP-A 101670; U.S. Pat. No. 4,683,000; U.S. Pat. No. 4,678,500; U.S. Pat. No. 4,786,311).

The urethanes of the formula (III) are obtained according to a novel and inventive process, if amines of the general formula (IV)

in which $R^2$, X, Y and Z have the abovementioned meaning, are reacted with chloroformic acid esters of the general formula (V)

in which $R^3$ has the abovementioned meaning, optionally in the presence of an acid acceptor, such as, for example, sodium (hydrogen) carbonate, potassium (hydrogen) carbonate or potassium tert-butylate, and optionally in the presence of a diluent, such as, for example, cyclohexane, methylcyclohexane, benzene, toluene, xylene, chlorobenzene, diisopropyl ether, dibutyl ether, diisobutyl ether, methyl tert-butyl ether, tetrahydrofuran, dioxane, glycol dimethyl ether, acetone, methyl ethyl ketone, methyl isobutyl ketone, methyl, ethyl, propyl or butyl acetate, acetonitrile or propionitrile, at temperatures between 0° C. and 150° C. (cf. the Preparation Examples).

The process according to the invention is carried out using alkali metal hydroxides or alcoholates or alkaline earth metal hydroxides or alcoholates. Preferred are lithium, sodium, potassium, magnesium and calcium hydroxide, sodium, potassium and magnesium methylate and ethylate, sodium and potassium propylate, isopropylate, butylate, isobutylate, sec-butylate and tert-butylate.

Particularly preferred are sodium and potassium methylate, sodium and potassium ethylate and also sodium and potassium hydroxide.

The process step according to the invention for preparing the sulphonamide salts of the formula (IIa) is preferably carried out in the presence of a diluent. In this context, suitable diluents are in particular organic solvents. These include preferably aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl and ethyl acetate, nitriles such as, for example, acetonitrile and propionitrile, amides such as, for example, dimethylformamide, dimethylacetamide and N-methylpyrrolidone, as well as alcohols such as methanol, ethanol, propanol, isopropanol, butanol, isobutanol, sec-butanol and tert-butanol as well as water. Water and alcohols such as methanol and ethanol are in this context very particularly preferred.

The reaction temperatures in the process step according to the invention for preparing the sulphonamide salts of the formula (IIa) may be varied over a wide range. In general, temperatures between −20° C. and +150° C., preferably between 0° C. and 120° C., are used.

The final step of the process according to the invention, i.e. the reaction of the sulphonamide salts of the formula (IIa) with the urethanes of the formula (III), is preferably carried out in the presence of a diluent. In this context, suitable diluents are in particular aprotic organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl and ethyl acetate, nitriles such as, for example, acetonitrile and propionitrile, amides such as, for example, dimethylformamide, dimethylacetamide and N-methylpyrrolidone as well as dimethyl sulphoxide, tetramethylene sulphone and hexamethylphosphoric acid triamide.

In this context ketones such as methyl isobutyl ketone and nitriles such as acetonitrile are very particularly preferred.

In the final step of the process according to the invention, the reaction temperatures may be varied over a wide range. In general, temperatures between −20° C. and +150° C., preferably temperatures between 0° C. and 100° C., are used.

The process according to the invention is generally carried out at atmospheric pressure. It is, however, also possible to work at increased or reduced pressure—in general between 0.1 bar and 10 bar.

To carry out the process according to the invention, in general between 0.9 and 1.5, preferably between 0.95 and 1.20 mol or molar equivalent of an alkali metal hydroxide or alcoholate or of an alkaline earth metal hydroxide or alcoholate and between 0.9 and 1.2, preferably between 0.95 and 1.10 mol of a urethane of the formula (III) are employed relative to 1 mol of sulphonamide of the formula (II).

In a preferred embodiment of the process according to the invention, the sulphonamide of the formula (II) is introduced into an organic diluent, and the alkali metal hydroxide or alcoholate or the alkaline earth metal hydroxide or alcoholate is metered in while stirring. The mixture is then stirred for some time and then concentrated under reduced pressure. The residue, which essentially contains the sulphonamide salt of the formula (IIa), is taken up in a suitable diluent and the urethane of the formula (III) is then added while stirring.

In a further preferred embodiment of the process according to the invention, the sulphonamide of the formula (II) is stirred with the aqueous solution of the equivalent quantity of an alkali metal or alkaline earth metal hydroxide until it is practically completely dissolved. Then undissolved components are optionally filtered off and an organic solvent, preferably methyl isobutyl ketone or toluene, is added to the solution. The water is then removed by azeotropic distillation. The urethane of the formula (III) is then added to the remaining solution, preferably at temperatures between 60° C. and 90° C., and the reaction mixture is stirred until the reaction is complete.

Once the reaction is complete, working-up can be carried out in a conventional manner (cf. the Preparation Examples).

The sulphonylurea salts of the formula (I) to be prepared by the process according to the invention may be employed as selective herbicides (cf. EP-A 251 079 and EP-A 433 779).

PREPARATION EXAMPLES

Example 1

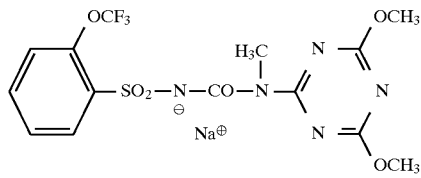

12.1 g (50.2 mmol) of 2-trifluromethoxy-benzenesulphonamide are taken up in 50 ml of methanol and 9.1 g of a 30% strength solution of sodium methylate in methanol (50.6 mmol NaOCH$_3$) are added at 20° C. with stirring. The mixture is then stirred at 20° C. for a further 2 hours and subsequently concentrated in a water jet vacuum. The residue is taken up in toluene and concentrated once again. The residue is then taken up in 100 ml of acetonitrile and 14.5 g (45.8 mmole) of phenyl N-methyl-N-(4,6-dimethoxy-1,3,5-triazin-2-yl)-carbamate are added with stirring at 20° C. After some time, a light yellow, almost clear solution results from the suspension, and from this solution a white solid gradually precipitates. After 12 hours the product is isolated by filtering off with suction.

19.9 g (93% of theory) of the sodium salt of 3-(4,6-dimethoxy-s-triazin-2-yl)-3-methyl-1-(2-trifluoromethoxy-phenylsulphonyl)-urea with a melting point of 224° C. are obtained (content according to HPLC: 98.3%).

In analogy to Example 1, and corresponding to the general description of the process according to the invention, the compounds of the formula (I) listed in Table 1 below, for example, may also be prepared.

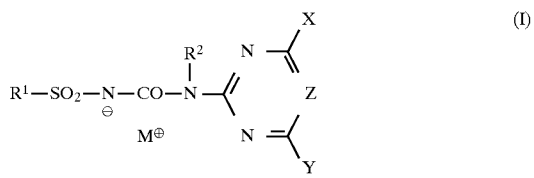

TABLE 1

Examples of compounds of the formula (I) to be prepared according to the invention

| Example No. | M$^+$ | R$^1$ | R$^2$ | X | Y | Z | m.p. [°C.] | Yield (% of theory) |
|---|---|---|---|---|---|---|---|---|
| 2 | Na$^+$ | (2-OCHF$_2$-phenyl) | CH$_3$ | OCH$_3$ | OCH$_3$ | N | 201 | 94 |
| 3 | Na$^+$ | (2-CF$_3$-benzyl) | CH$_3$ | OCH$_3$ | OCH$_3$ | N | >230 | 95 |
| 4 | Na$^+$ | (2-OCF$_3$-benzyl) | CH$_3$ | OCH$_3$ | OCH$_3$ | N | 188 | 88 |

TABLE 1-continued

Examples of compounds of the formula (I) to be prepared according to the invention

| Example No. | M⁺ | R¹ | R² | X | Y | Z | m.p. [°C.] | Yield (% of theory) |
|---|---|---|---|---|---|---|---|---|
| 5 | Na⁺ | 2-(OCF₃)-phenyl | CH₃ | CH₃ | OCH₃ | N | 194 | 87 |
| 6 | Na⁺ | 2-(OCF₃)-benzyl (-CH₂-) | CH₃ | CH₃ | OCH₃ | N | 200 | 88 |
| 7 | Na⁺ | 2-(OCF₃)-phenyl | H | OCH₃ | OCH₃ | CH | 190 | 59 |
| 8 | Na⁺ | 2-(CH₃)-phenyl | CH₃ | OCH₃ | OCH₃ | N | 135 | 76 |
| 9 | Na⁺ | 2-(OCH₃)-phenyl | CH₃ | OCH₃ | OCH₃ | N | 165 | 78 |
| 10 | Na⁺ | 2-Br-phenyl | CH₃ | OCH₃ | OCH₃ | N | 195 | 90 |
| 11 | Na⁺ | 2-(SCH₃)-phenyl | CH₃ | OCH₃ | OCH₃ | N | 130 | 91 |
| 12 | Na⁺ | 3-CON(CH₃)₂-pyridin-2-yl | CH₃ | OCH₃ | OCH₃ | N | 220 | 75 |
| 13 | Na⁺ | 2-OCH₃-5-(H₃CO)-phenyl | CH₃ | OCH₃ | OCH₃ | N | 225 | 88 |

The compound obtained according to Example 1 may, for example, also be prepared as follows:

Example 1a

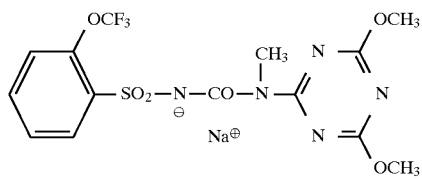

14.4 g (60 mmol) of 2-trifluoromethoxy-benzenesulphonamide are stirred with a solution of 2.4 g (60 mmol) of sodium hydroxide in 50 ml of water at 20° C. until solution is practically complete. After filtration, 150 ml of methyl isobutyl ketone are added to the clear solution and the water is removed by azeotropic distillation. Subsequently, 18.8 g (60.6 mmol) of phenyl N-methyl-N-(4,6-dimethoxy-1,3,5-triazin-2-yl)-carbamate are added to the remaining solution at 70° C. to 90° C. A clear solution is formed from which the product precipitates voluminously after a short period of time. In order to be able to stir more readily, the solution is diluted to 500 ml (with methyl isobutyl ketone) and the mixture is stirred at 20° C. for 12 hours. The product is then isolated by filtration with suction.

24 g (84% of theory) of the sodium salt of 3-(4,6-dimethoxy-s-trazin-2-yl)-3-methyl-1-(2-trifluoromethoxy-phenylsulphonyl)-urea with a melting point of 224° C. are obtained (content according to HPLC: 96.7%).

The compound listed in Table 1 as Example 2 may, for example, be prepared as follows:

Example 2a

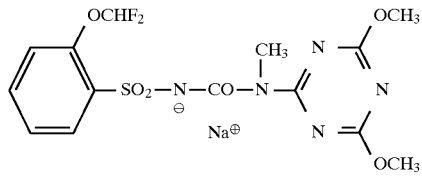

6.7 g (30 mmol) of 2-difluoromethoxy-benzenesulphonamide are stirred with a solution of 1.2 g (30 mmol) of sodium hydroxide in 30 ml of water until solution is practically complete. After filtration, 300 ml of methyl isobutyl ketone are added to the clear solution and the water is removed by azeotropic distillation. Subsequently, 9.3 g (30 mmol) of phenyl N-methyl-N-(4,6-dimethoxy-1,3,5-triazin-2-yl)-carbamate are added to the remaining mixture at 70° C. to 80° C. The reaction mixture is stirred at 20° C. for a further 12 hours; the resulting crystalline product is then isolated by filtration with suction.

11.4 g (77% of theory) of the sodium salt of 3-(4,6-dimethoxy-s-triazin-2-yl)-3-methyl-1-(2-difluoromethoxy-phenylsulphonyl)-urea with a melting point of 201° C. are obtained (content according to HPLC: 88.9%).

Starting materials of the formula (III):

Example (III-1)

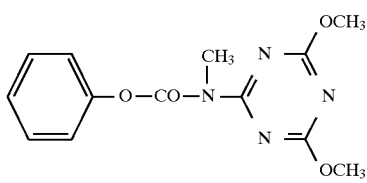

3.7 g (0.033 mol) of K t-butylate are added to 5.0 g (0.0294 mol) of 2-methylamino-4,6-dimethoxy-1,3,5-triazine in 100 ml of tetrahydrofuran. While stirring thoroughly, 5.1 g (0.0326 mol) of phenyl chloroformate are rapidly added dropwise, during which time the reaction mixture is kept at about 25° C. by cooling. After 12 h at 20° C., the mixture is concentrated in vacuo, taken up in methylene chloride and washed to neutrality with water. After drying with magnesium sulphate, the mixture is concentrated, and the residue stirred with ether/petroleum ether (1:1). The precipitated crystalline product is filtered off with suction and dried. Yield: 6.6 g (73% of theory) of phenyl N-methyl-N-(4,6-dimethoxy-1,3,5-triazin-2-yl)-carbamate with a m.p. of 90° C.

Example (III-2)

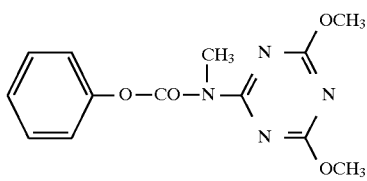

10.2 g (0.0651 mol) of phenyl chloroformate are added dropwise with stirring at 80° C. and within 1.5 hours to a mixture of 5.0 g (0.0294 mol) of 2-methylamino-4,6-dimethoxy-1,3,5-triazine and 5.5 g (0.0655 mol) of sodium hydrogen carbonate in 100 ml of cyclohexane. The mixture is heated for 12 h under reflux in a water separator, cooled and concentrated. The residue is taken up in methylene chloride and washed to neutrality with water, dried and concentrated. After stirring with ether/petroleum ether 1:1, 5.3 g of white crystals (59% of theory) phenyl N-methyl-N-(4,6-dimethoxy-1,3,5-triazin-2-yl)-carbamate with a m.p. of 90° C. are obtained.

The compounds of the formula (III) listed in Table 2 below may also, for example, be prepared in an analogous manner.

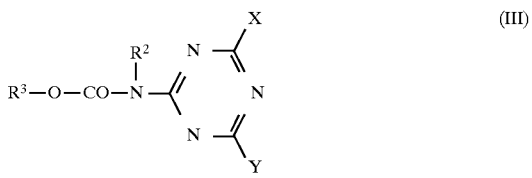

TABLE 2

Examples of compounds of the formula (III)

| Example No. | $R^2$ | $R^3$ | X | Y | Z | Melting Point (°C.) |
|---|---|---|---|---|---|---|
| III-3 | CH$_3$ | C$_6$H$_5$ | CH$_3$ | OCH$_3$ | N | 82 |
| III-4 | CH$_3$ | C$_6$H$_5$—CH$_2$ | OCH$_3$ | OCH$_3$ | N | 77 |
| III-5 | CH$_3$ | C$_2$H$_5$ | OCH$_3$ | OCH$_3$ | N | 45 |
| III-6 | CH$_3$ | CH$_3$ | OCH$_3$ | OCH$_3$ | N | 69 |
| III-7 | C$_2$H$_5$ | C$_6$H$_5$ | CH$_3$ | CH$_3$ | N | |
| III-8 | C$_2$H$_5$ | C$_6$H$_5$ | CH$_3$ | OCH$_3$ | N | |
| III-9 | C$_2$H$_5$ | C$_6$H$_5$ | OCH$_3$ | OCH$_3$ | N | 61–62 |
| III-10 | C$_3$H$_7$-n | C$_6$H$_5$ | OCH$_3$ | OCH$_3$ | N | |
| III-11 | C$_3$H$_7$-i | C$_6$H$_5$ | OCH$_3$ | OCH$_3$ | N | |
| III-12 | CH$_2$—CH=CH$_2$ | C$_6$H$_5$ | OCH$_3$ | OCH$_3$ | N | |
| III-13 | C$_3$H$_7$-n | C$_6$H$_5$ | CH$_3$ | OCH$_3$ | N | |
| III-14 | C$_3$H$_7$-i | C$_6$H$_5$ | CH$_3$ | OCH$_3$ | N | |
| III-15 | CH$_2$—C≡CH | C$_6$H$_5$ | OCH$_3$ | OCH$_3$ | N | |
| III-16 | CH$_2$—C≡CH | C$_6$H$_5$ | CH$_3$ | OCH$_3$ | N | |
| III-17 | CH$_2$—C$_6$H$_5$ | C$_6$H$_5$ | OCH$_3$ | OCH$_3$ | N | |

The compound obtained according to Example (III-2) may also, for example, be prepared as follows:

Example (III-2a)

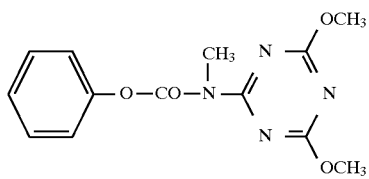

A mixture of 89.6 g (0.52 mol) of 2-methylamino-4,6-dimethoxy-1,3,5-triazine, 84 g (1.0 mol) of sodium hydrogen carbonate and 800 ml of butyl acetate is heated under reflux in a water separator and a solution of 102 g (0.65 mol) of phenyl chloroformate in 500 ml of butyl acetate is added dropwise during the course of 8 hours. After a further hour under reflux, the mixture is allowed to cool and the reaction solution is washed with water. The wash water is neutralised with 2N hydrochloric acid and re-extracted with butyl acetate. The combined organic solutions are dried with sodium sulphate and filtered. The filtrate is concentrated and the oily residue is taken up in methylcyclohexane and stirred vigorously. The crystalline product resulting from this is isolated by filtration with suction.

132 g (80% of theory) of phenyl N-methyl-N-(4,6-dimethoxy-1,3,5-triazin-2-yl)-carbamate with a melting point of 90° C. are obtained.

Example (III-2b)

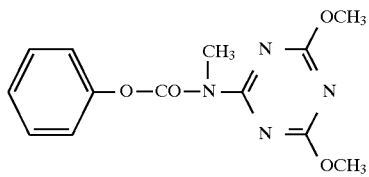

A mixture of 17 g (0.1 mol) of 2-methylamino-4,6-dimethoxy-1,3,5-triazine, 12.5 g (0.15 mol) of sodium hydrogen carbonate and 125 ml of methyl isobutyl ketone is heated under reflux in a water separator and a solution of 23.5 g (0.15 mol) of phenyl chloroformate in 25 ml of methyl isobutyl ketone is added dropwise during the course of 2.5 hours. After a further 2.5 hours under reflux, the mixture is cooled to 30° C. and washed with 1% strength sodium carbonate solution. The aqueous phase is re-extracted with methyl isobutyl ketone. The combined organic solutions are dried with sodium sulphate and filtered. The filtrate is concentrated and the resulting residue is recrystallised from cyclohexane.

21.8 g (72% of theory) of phenyl N-methyl-N-(4,6-dimethoxy-1,3,5-triazin-2-yl)-carbamate with a melting point of 90° C. are obtained.

Example (III-2c)

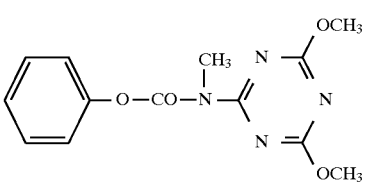

172 g (1.0 mol) of 2-methylamino-4,6-dimethoxy-1,3,5-triazine and 168 g (2.0 mol) of sodium hydrogen carbonate are heated under reflux in 1 liter of toluene in a water separator. 235 g (1.5 mol) of phenyl chloroformate are added dropwise over the course of 5 hours and the complete reaction mixture is then stirred for a further hour under reflux. After cooling to 40° C., the mixture is filtered and the solvent is carefully distilled off from the filtrate in vacuo.

348 g (91% of theory) of phenyl N-methyl-N-(4,6-dimethoxy-1,3,5-triazin-2-yl)-carbamate are obtained as a yellowish solid.

It will be appreciated that the instant specification and claims are set forth by way of illustration and not limitation, and that various modifications and changes may be made without departing from the spirit and scope of the present invention.

I claim:

1. A process for preparing sulphonylurea salts of the formula

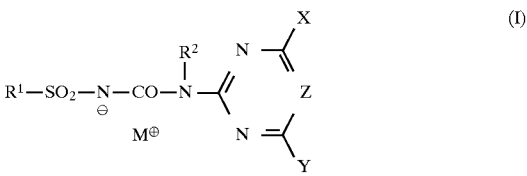

in which

M$^+$ represents an alkali metal ion or an alkaline earth metal ion equivalent,

R$^1$ represents in each case optionally substituted aryl, aralkyl or heteroaryl, R$^2$ represents hydrogen or in each case optionally substituted alkyl, alkenyl, alkinyl or aralkyl, X represents hydrogen, halogen or alkyl, alkoxy, alkylthio or alkylamino, in each case optionally substituted by halogen or alkoxy, Y represents hydrogen, halogen or alkyl or alkoxy, in each case optionally substituted by halogen, and Z represents nitrogen, a CH group or a C-halogen group, wherein sulphonamides of the formula $$R^1-SO_2-NH_2 \qquad (II)$$

in which

R¹ has the abovementioned meaning, are first reacted with alkali metal hydroxides or alcoholates or with alkaline earth metal hydroxides or alcoholates optionally in the presence of a diluent at temperatures between −20° C. and +150° C. (step 1)

and the sulphonamide salts thus formed, of the formula

R¹—SO₂—NH—M⁺     (IIa)

in which

M and R¹ have the abovementioned meaning, are then reacted with urethanes (carbamates) of the formula

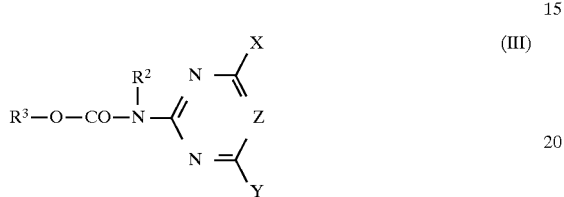

(III)

in which

R², X, Y and Z have the abovementioned meaning and
R³ represents alkyl, aralkyl or aryl, optionally in the presence of a diluent at temperatures between −20° C. and +150° C. (step 2) and the products of the formula (I) are isolated by conventional methods.

2. A process according to claim 1 for preparing compounds of formula (I), wherein M⁺ represents a lithium, sodium or potassium ion, or a magnesium or calcium ion equivalent, R¹ represents in each case optionally substituted phenyl, naphthyl, benzyl, pyridyl, thienyl or pyrazolyl, where the substituents are selected from the group consisting of halogen, carboxyl, cyano, carbamoyl, nitro, amino, $C_1$–$C_4$-alkyl, $C_1$–$C_4$-halogenoalkyl, $C_1$–$C_4$-alkoxy-$C_1$–$C_4$-alkyl, $C_1$–$C_4$-alkoxy, $C_1$–$C_4$-halogenoalkoxy, $C_1$–$C_4$-alkoxy-$C_1$–$C_4$-alkoxy, $C_1$–$C_4$-alkylthio, $C_1$–$C_4$-alkylsulphinyl, $C_1$–$C_4$-alkylsulphonyl, di-($C_1$–$C_4$-alkyl)-amino-sulphonyl, N-$C_1$–$C_4$-alkoxy-N-$C_1$–$C_4$-alkyl-amino-sulphonyl, phenyl, phenoxy, $C_1$–$C_4$-alkoxy-carbonyl, $C_1$–$C_4$-halogenoalkoxy-carbonyl, $C_1$–$C_2$-alkoxy-$C_1$–$C_2$-carbonyl, and di-($C_1$–$C_4$-alkyl)-amino-alkoxy-carbonyl, R² represents hydrogen, $C_1$–$C_6$-alkyl which is optionally substituted by fluorine, cyano, $C_1$–$C_4$-alkoxy or $C_1$–$C_4$-alkylthio, $C_3$–$C_6$-alkenyl and $C_3$–$C_6$-alkinyl which are optionally substituted by fluorine or chlorine, or phenyl-$C_1$–$C_2$-alkyl which is optionally substituted in the phenyl moiety by fluorine, chlorine, nitro, cyano, methyl, methoxy or $C_1$–$C_2$-alkoxycarbonyl, X represents hydrogen, halogen or $C_1$–$C_4$-alkyl, $C_1$–$C_4$-alkoxy, $C_1$–$C_4$-alkylthio or $C_1$–$C_4$-alkylamino, which are optionally substituted by halogen or $C_1$–$C_4$-alkoxy, Y represents hydrogen, halogen or $C_1$–$C_4$-alkyl or $C_1$–$C_4$-alkoxy, which are optionally substituted by halogen, and Z represents nitrogen or a CH group.

3. A process according to claim 1 for preparing compounds of formula (I), wherein M⁺ represents a sodium ion or potassium ion, R¹ represents a phenyl or benzyl which are substituted in the ortho position by fluorine, chlorine, bromine, methyl, ethyl, trifluoromethyl, methoxy, ethoxy, difluoromethoxy, trifluoromethoxy, chloroethoxy, methoxyethoxy, ethoxyethoxy, methylthio, ethylthio, propylthio, methylsulphinyl, ethylsulphinyl, propylsulphinyl, methylsulphonyl, ethylsulphonyl, propylsulphonyl, dimethylaminosulphonyl, diethylaminosulphonyl, N-methoxy-N-methyl-aminosulphonyl, phenyl, methoxycarbonyl, ethoxycarbonyl, propoxycarbonyl, isopropoxycarbonyl, chloroethoxycarbonyl, methoxyethoxycarbonyl, dimethylaminocarbonyl or diethylaminocarbonyl and are optionally substituted in a another position by halogen, or represents 3-dimethylaminocarbonyl-pyridin-2-yl or 3-ethylsulphonyl-pyridin-2-yl, 2-methoxycarbonyl-thiophen-3-yl or 1-methyl-4-methoxycarbonyl-pyrazol-5-yl, 1-methyl-4-ethoxycarbonyl-pyrazol-5-yl, 1-methyl-3-chloro-4-methoxycarbonyl-pyrazol-5-yl, 1-methyl-3-chloro-4-ethoxycarbonyl-pyrazol-5-yl or 1-pyridyl-4-methoxycarbonyl-pyrazol-5-yl, R₂ represents hydrogen or methyl, X represents hydrogen, chlorine, methyl, ethyl, trichloromethyl, trifluoromethyl, methoxymethyl, methoxy, ethoxy, difluoromethoxy, fluoromethoxy, difluoroethoxy, trifluoroethoxy, methoxyethoxy, methylthio, ethylthio, methylamino or ethylamino, Y represents hydrogen, chlorine, methyl, ethyl, trifluoromethyl, methoxy, ethoxy or difluoromethoxy, and Z represents nitrogen or a CH group.

4. A process according to claim 1, wherein the 1st process step is carried out at temperatures between 0° C. and 120° C.

5. A process according to claim 1, wherein the 2nd process step is carried out at temperatures between 0° and 100° C.

6. A process according to claim 1, wherein the 1st process step water or an alcohol is employed as the diluent.

7. A process according to claim 1, wherein the 2nd process step a ketone or a nitrile is employed as the diluent.

8. A process according to claim 1, wherein the sulphonamide of the formula (II) is introduced into an organic diluent and the alkali metal hydroxide or alcoholate or the alkaline earth metal hydroxide or alcoholate is metered in while stirring, the mixture is then stirred for some time and then concentrated under reduced pressure, and the residue which essentially contains the sulphonamide salt of the formula (IIa) is taken up in a suitable diluent and the urethane of the formula (III) is then added while stirring.

9. Process for preparing urethanes of the formula (III),

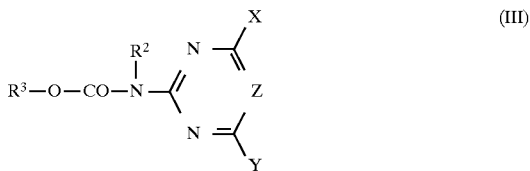

(III)

in which

R² represents hydrogen or in each case optionally substituted alkyl, alkenyl, alkinyl or aralkyl, X represents hydrogen, halogen or alkyl, alkoxy, alkylthio or alkylamino, in each case optionally substituted by halogen or alkoxy, Y represents hydrogen, halogen or alkyl or alkoxy, in either case optionally substituted by halogen, Z represents nitrogen, a CH grouping or a C-halogen grouping, and $R^3$ represents alkyl, aralkyl or aryl, characterised in that amines of the general formula (IV)

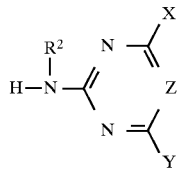 (IV)

in which $R^2$, X, Y and Z have the abovementioned meaning, are reacted with chloroformic acid esters of the general formula (V)

$$R^3-O-CO-Cl \qquad (V)$$

in which $R^3$ has the abovementioned meaning, optionally in the presence of an acid acceptor, and optionally in the presence of a diluent, at temperatures between 0° C. and 150° C.

10. A process according to claim 6, wherein the alcohol is methanol or ethanol.

11. A process according to claim 7, wherein the ketone is methyl isobutyl ketone or the nitrile is acetonitrile.

* * * * *

UNITED STATES PATENT AND TRADEMARK OFFICE
CERTIFICATE OF CORRECTION

PATENT NO : 5,886,176
DATED : March 23, 1999
INVENTOR(S): Klaus-Helmut MULLER

It is certified that error appears in the above-identified patent and that said Letters Patent is hereby corrected as shown below:

Title page [75]    Delete "Düsseldorff" and substitute -- Düsseldorf--

Signed and Sealed this

Twenty-seventh Day of February, 2001

Attest:

NICHOLAS P. GODICI

Attesting Officer    Acting Director of the United States Patent and Trademark Office